US00PP35001P3

(12) United States Plant Patent
Scalzo et al.

(10) Patent No.: US PP35,001 P3
(45) Date of Patent: Feb. 28, 2023

(54) BLUEBERRY PLANT NAMED 'C15-270'

(50) Latin Name: *Vaccinium corymbosum*
Varietal Denomination: C15-270

(71) Applicants: Costa Berry International Pty Ltd, Ravenhall (AU); FLORIDA FOUNDATION SEED PRODUCERS, INC., Marianna, FL (US)

(72) Inventors: Jessica Scalzo, Corindi Beach (AU); James W. Olmstead, Aptos, CA (US)

(73) Assignees: COSTA BERRY INTERNATIONAL PTY LTD, Revenhall (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/803,047

(22) Filed: Jan. 26, 2022

(65) Prior Publication Data

US 2022/0248582 P1 Aug. 4, 2022

Related U.S. Application Data

(60) Provisional application No. 63/206,157, filed on Jan. 29, 2021.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./156, 157
See application file for complete search history.

*Primary Examiner* — Karen M Redden
(74) *Attorney, Agent, or Firm* — Baker & McKenzie LLP

(57) ABSTRACT

The new blueberry plant variety 'C15-270' is provided. 'C15-270' is a commercial variety intended for the fresh market. The variety is produced from a cross of unpatented parents 'FL12-082' and 'FL12-069'.

4 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'C15-270'.

BACKGROUND OF THE INVENTION

The new variety 'C15-270' was selected from a population of seedlings derived from crossing the blueberry varieties known as 'FL12-082' (unpatented seed parent) and the variety known as 'FL12-069' (unpatented pollen parent). The cross was made in 2012 in Florida, USA and the seed was sown and grown in Corindi Beach, New South Wales, Australia. The new variety was selected in 2015 from among plants located on land at Corindi Beach and assigned the breeding code 'C15-270'. Plants of 'C15-270' were propagated by cuttings for further evaluation and resulted to be uniform and stable. The new variety showed distinctive traits such as evergreen, with fruit of good flavor, large fruit size, and firmness.

SUMMARY OF THE INVENTION

The new variety 'C15-270' was originated from a cross of 'FL12-082' (unpatented seed parent) and the variety known as 'FL12-069' (unpatented pollen parent) in 2012 in Florida, USA.

The new blueberry variety resulted from seedlings produced in a controlled breeding programme. The cross was made in 2012 in Florida, USA and the seed was sown and grown on in Corindi Beach, New South Wales, Australia.

The new variety was selected in 2015 from among plants located on land at Corindi Beach and has since been named 'C15-270'. Since then plants of 'C15-270' were propagated by cuttings for further evaluation and confirmed to be uniform and stable. Asexual reproduction of the new variety 'C15-270' by cutting propagation since 2015 at Corindi Beach, New South Wales, Australia has demonstrated that the new variety reproduces true to type plants.

The new variety was selected in 2015 as a single plant within a population of seedlings resulting from controlled cross of *Vaccinium* varieties. The seedling population was planted in an experimental block in the field at Corindi Beach, New South Wales, Australia and the selection of the new variety took place in the same block. Selection criteria were a combination of late cropping season, low chilling requirement, strong plant vigour, non-deciduous type of plant (evergreen), large fruit size, good fruit flavor, and very firm fruit. The new variety was subsequently evaluated for five years at the commercial farm at Corindi Beach, New South Wales, Australia.

The following characteristics of the new variety have been repeatedly observed and can be used to distinguish 'C15-270' as a new and distinct variety of *Vaccinium corymbosum* hybrid:

1. Non-deciduous (Evergreen)
2. Late season crop
3. Strong plant vigour
4. High yields
5. Low chilling requirement
6. Excellent firmness and good flavor The new blueberry variety 'C15-270' has maintained its distinguished characteristics throughout successive asexual propagation. The variety has been repeatedly asexually reproduced through softwood cuttings in New South Wales, Australia and the clones are phenotypically identical to the original plant.

BRIEF DESCRIPTION OF THE DRAWINGS

The accompanying photographic illustration shows typical specimens in full color of the foliage and fruit of the new variety 'C15-270'. The colors are as nearly true as is reasonably possible in a color representation of this type.

Figure 1:
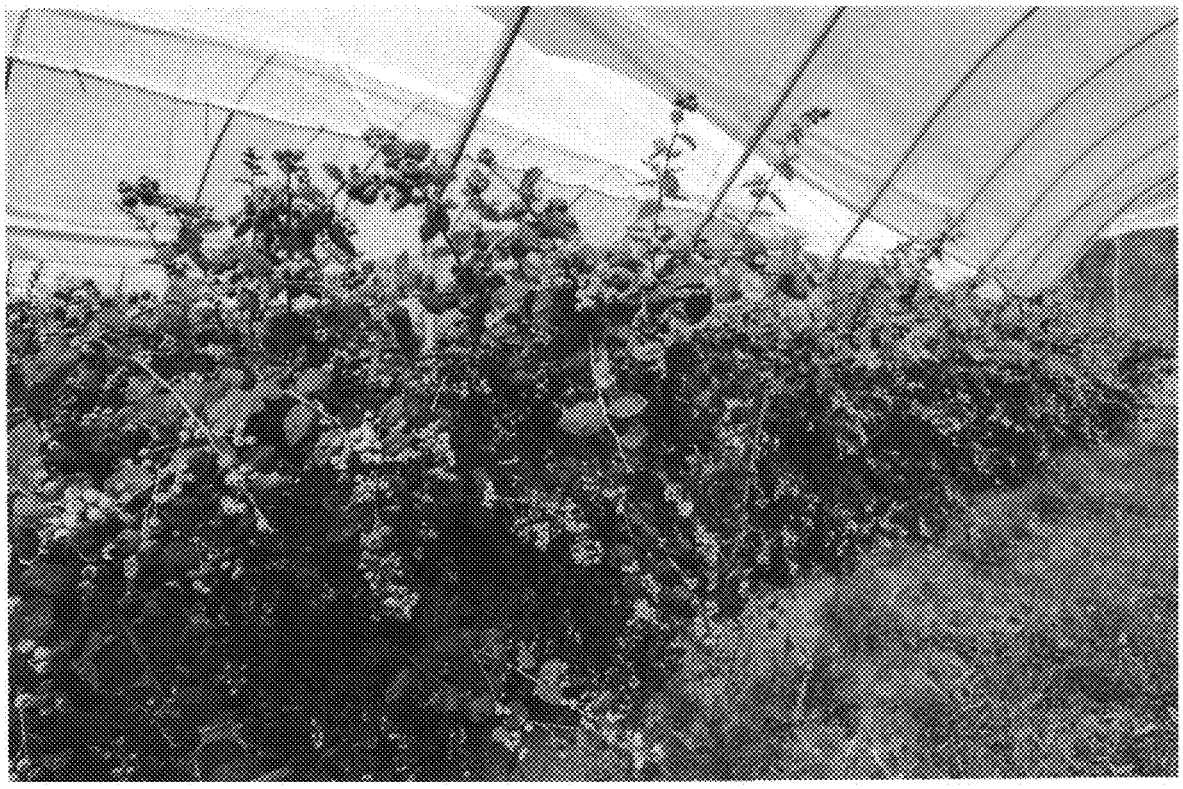
FIG. 1 is a photograph of three-year-old plants of the new variety 'C15-270'.
Figure 2:
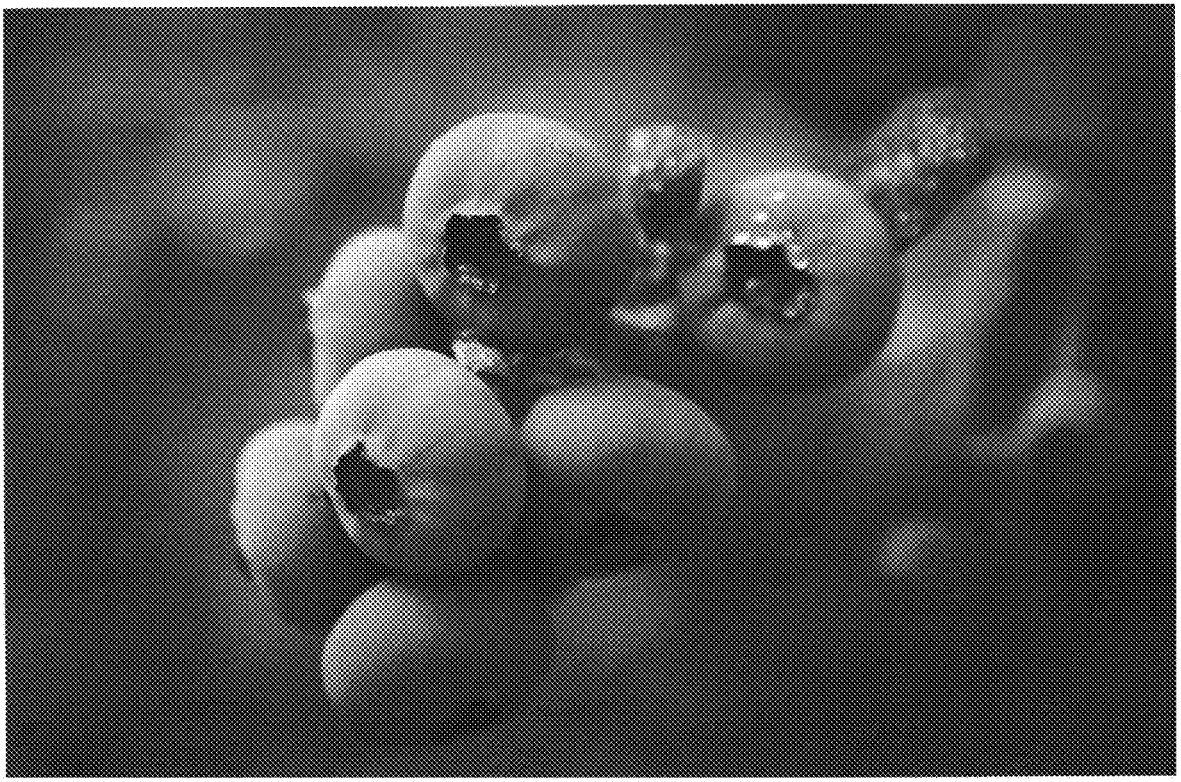
FIG. 2 is a photograph of the typical fruit cluster of the new variety 'C15-270'.
Figure 3:
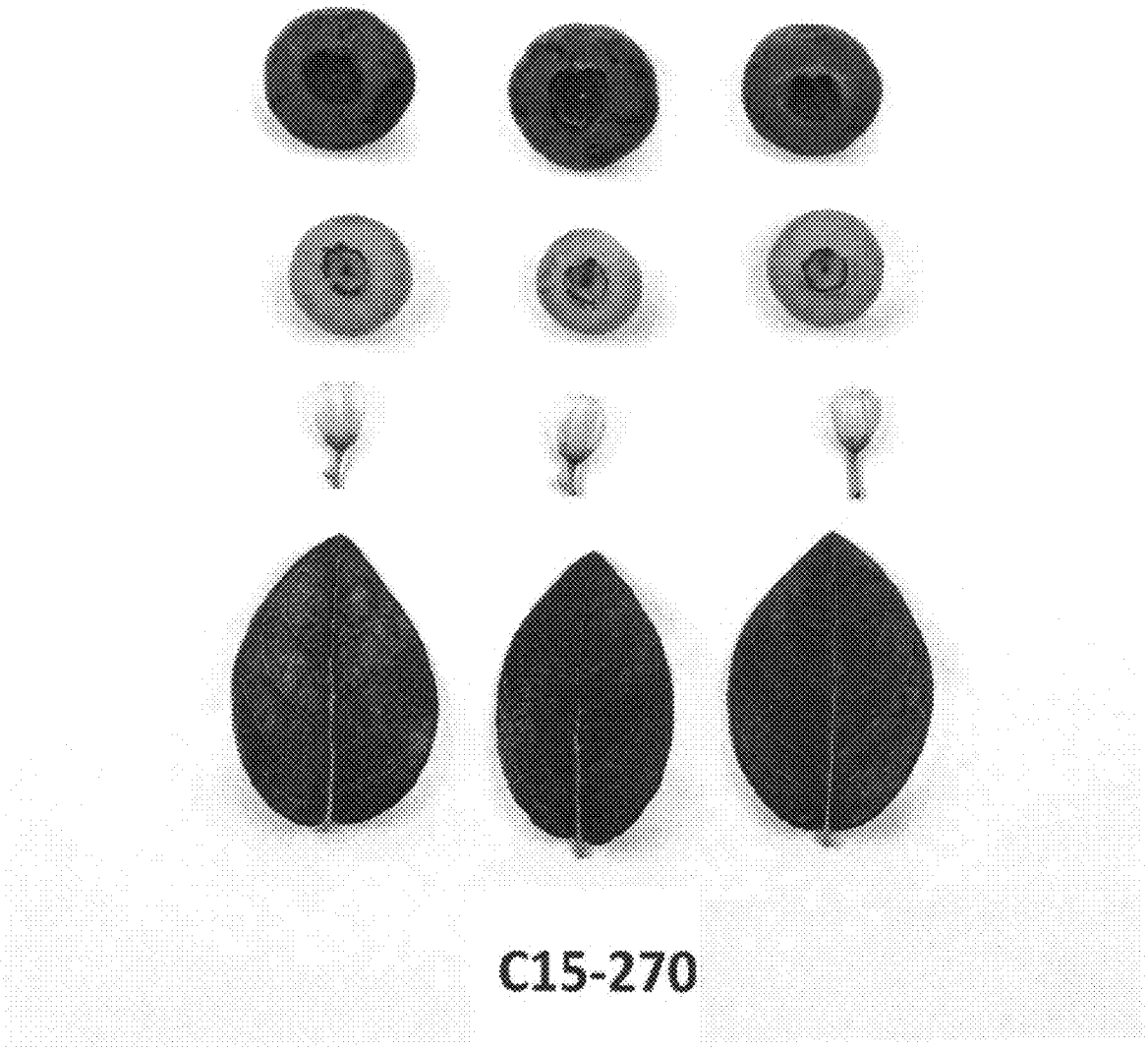
FIG. 3 is a photograph of the botanical parts (ripe fruit, green fruit, flowers and leaves) of the new variety 'C15-270'.
Figure 4:
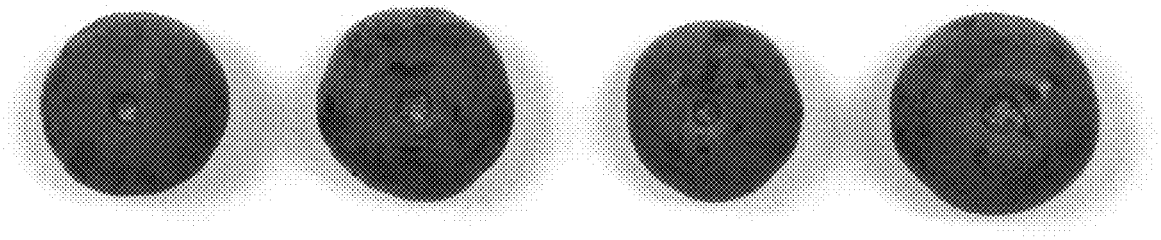
FIG. 4 is a photograph showing the medium to large pedicel scar of the new variety 'C15-270'.

The colors in the photographs are as close as possible with the photographic and printing technology utilized. The color values cited in the detailed botanical description accurately describe the colors of the new blueberry variety.

DETAILED BOTANICAL DESCRIPTION

The following detailed description sets forth the distinctive characteristics of 'C15-270'. The data which defines these characteristics was collected from asexual reproductions of the original selection. Dimensions, sizes, colors, and other characteristics are approximations and averages set forth as accurately as possible. For all traits data was collected from 3 plant parts across 6 randomly selected plants. For the traits relating to fruits (e.g., fruit weight, firmness, brix, acidity) the data is an average across twenty fruits collected randomly. The plant history was taken on plants approximately 3 years of age, and the descriptions relate to plants grown in the field in Corindi Beach, New South Wales, 2456 Australia. Descriptions of fruit characteristics were made on fruit grown in Corindi Beach, New South Wales, 2456 Australia. Color designations are from the 2007 edition of The Royal Horticultural Society ("R.H.S."). 'C15-270' has not been observed under all possible environments. The phenotype may vary slightly with different growing environments such as temperature, light, fertility, soil pH, moisture and maturity levels, but without any change in the genotype.

Classification:

a. *Family*.—Ericaceae.
b. *Genus*.—*Vaccinium*.
c. *Species*.—*Corymbosum* hybrid.
d. *Common name*.—Blueberry.

Parentage:

*Female parent*.—Unpatented selection 'FL12-082'.
*Male parent*.—Unpatented selection 'FL12-069'.

Market class: Fresh market.

PLANT

General:

*Parentage*.—FL12-082 x FL12-069.
*Plant height*.—1.45 m.
*Plant width*.—1.26 m.
*Growth habit*.—Semi-upright.
*Growth*.—Strong vigour.
*Mature cane length*.—0.60 m.
*Mature cane width*.—15.8 mm.
*Mature cane color*.—Grey-brown group, similar to 199B, with streak of grey-brown group similar to 199D.
*Bark texture*.—Medium (texture between rough and smooth).
*Fall color on new shoots*.—The base color is green group, similar to 137C and with over color, red-purple group, similar to 59A.
*Surface texture of new wood*.—Smooth.
*Internode length on strong, new shoots*.—33.3 mm.
*Fruiting wood in length*.—39.0 cm.
*Productivity*.—Very high yield. Average of 7 Kg per plant (estimated equivalent production is 15.4 pounds per plant) from 3 year old plants when growing in 17 L pots at Corindi Beach, NSW. The plants are spaced at 0.7 m apart along the row and 2.5 m between the rows, which gives an estimated plant density of 5700 plants per hectare.
*Cold hardiness*.—Low chill (USDA plant hardiness Zone 4).
*Cold tolerance*.—Low.
*Chilling requirement*.—Low, estimated between 150 and 300 hours.
*Resistance to disease*.—Resistant to blueberry leaf rust (*Thekopsora minima*).
*Heat tolerance*.—Moderately resistant to heat.
*Leafing*.—Overall strong leafing, and plant retains leaves during the winter.
*Twigginess*.—Low.

FOLIAGE

General:

*Leaf color* (*top side*).—Green group, similar to 139A.
*Leaf color* (*under side*).—Green group, similar to 147B.
*Leaf arrangement*.—Alternate.
*Leaf shape*.—Elliptic.
*Leaf margins*.—Entire.
*Leaf venation*.—Reticulate.
*Leaf length*.—Short, average 52.4 mm.
*Leaf width*.—Broad, average 34.6 mm.
*Leaf length/width ratio*.—1.5.
*Shape of the leaf apex*.—Acute.
*Shape of the leaf base*.—Cuneate.
*Leaf nectaries*.—Absent.
*Pubescence of upper side*.—Absent.
*Pubescence of lower side*.—Absent.
*Cross sectional profile*.—Flat.
*Longitudinal profile*.—Straight.
*Attitude*.—Horizontal.

Petioles:

*Length*.—Average 4.4 mm.
*Width*.—Average 1.45 mm.
*Color*.—Yellow green group, similar to 145B.
*Texture*.—Smooth.

FLOWERS

General:

*Time beginning of flowering*.—Late season (50% of anthesis estimated to be on the 1st of August, on 3 year old plants, cultivated at Corindi Beach, NSW).

*Flower shape*.—Urceolate.
*Flower fragrance*.—None perceptible.

Corolla:
*Shape*.—Urceolate.
*Color*.—White group, similar to NN155B.
*Length*.—8.8 mm.
*Width of widest region*.—8.9 mm.
*Petal texture*.—Smooth.
*Petal width* (*ridge to ridge*).—5.06 mm.
*Aperture diameter*.—4.8 mm.
*Anthocyanin coloration of corolla*.—Absent or very weak.
*Corolla ridges*.—Present.
*Protrusion of stigma*.—Present.

Inflorescence:
*Inflorescence length* (*excluding peduncle*).—Medium to short 13.9 mm.
*Inflorescence width*.—15.35 mm.
*Flower length* (*excluding pedicel*).—10.74 mm.
*Flower diameter*.—8.6 mm.
*Flower length/width ratio*.—1.25.
*Surface texture of peduncle*.—Rough.
*Color of peduncle*.—Yellow-green group, similar to 145B, with greyed-red group, similar to 182A on top.
*Length of flower pedicel*.—10.8 mm.
*Surface texture of pedicel*.—Medium (between rough and smooth).
*Color of pedicel*.—Yellow green group, similar to 146C.
*Number of flowers per cluster*.—8 (on average).
*Flower cluster density*.—Dense.
*Flowering interval on current year shoot*.—July to end August.
*Flowering interval on one-year old shoot*.—July to end August.

Calyx (with sepals):
*Diameter*.—6.44 mm.
*Height of sepal*.—2.39 mm.
*Shape of sepal*.—Deltoid.
*Shape of the sepal's apex*.—Acute.
*Margin of sepal*.—Entire.
*Texture of sepal's lower and upper side*.—Smooth.
*Color of sepal's lower side*.—Yellow green group, similar to 145B.
*Color of sepal's upper side*.—Yellow green group, similar to 144D.

Stamen:
*Length*.—7.6 mm.
*Number per flower*.—10.
*Filament color*.—Yellow-green group, similar to 145D.

Pistil:
*Length*.—12.3 mm.
*Length* (*including ovary*).—12.6 mm.
*Style: length* (*including stigma*).—10.5 mm.
*Style: color*.—Yellow-green group, similar to N144B.

Anther:
*Length*.—4.4 mm.
*Number*.—10.
*Color*.—Greyed-orange group, similar to 165B.

Pollen:
*Self compatibility*.—Yes (the variety shows a high degree of self-compatibility).
*Abundance*.—Abundant.
*Color*.—Yellow group, similar to 10A.

FRUIT

General:
*Time of fruit ripening*.—Late season, estimated 50% of the fruit ripe on the 1st week of October, on 3 year old plants, growing at Corindi Beach, NSW.
*Cluster density*.—Dense, range of 6-9 berries per cluster.
*Unripe fruit color*.—Yellow green group, similar to 144B.
*Ripe berry color*.—Blue group 103A.
*Berry surface wax abundance*.—Medium.
*Berry weight*.—Large berry, on average 3 g.
*Berry height from calyx to scar*.—13.6 mm.
*Berry diameter*.—18.9 mm.
*Berry shape*.—Oblate.
*Diameter of calyx basin*.—Medium to large (6.7 mm).
*Depth of calyx basin*.—Medium to deep.
*Fruit stem scar*.—Large.
*Sweetness when ripe*.—Medium to high (13 Brix).
*Firmness when ripe*.—Very firm, 209 g/mm, measured with FirmTech.
*Acidity when ripe*.—Medium to low (0.4%).
*Fruit flesh color*.—Yellow-green 145B.
*Storage quality*.—Low, similar to that of the bench mark variety 'Snowchaser' and average of 17 days.
*Suitability for mechanical harvesting*.—Not tested.
*Self-fruitfulness*.—Yes, with a proportion of fruit parthenocarpic.
*Uses*.—Fruit to be hand harvested for fresh market.

SEED

General:
*Seed abundance in fruit*.—Low, on average 9 seeds per fruit.
*Seed color*.—Greyed orange group, similar to 165A.
*Seed length*.—2.16 mm.

COMPARISON BETWEEN PARENTAL AND SIMILAR CULTIVARS

Table 1 below provides a comparison between 'C15-270' and similar cultivars:

TABLE 1

Comparison of 'C15-270' with similar cultivars

| Characteristics | 'C15-270' | 'C99-042' (U.S. Plant Pat. No. 20,695P2) | 'Snowchaser' (U.S. Plant Pat. No. 19,503P3) |
|---|---|---|---|
| Plant vigour | Strong | Weak to medium | Medium |
| Plant growth habit | Semi upright | Semi-upright to intermediate | Semi-upright |
| One year old shoot length of internodes | Medium | Very short to short | Short |
| Leaf length | Short | Short | Long |
| Leaf length (mm) | 52.4 ± 1.5 | 53.10 ± 0.8 | 61.50 ± 0.9 |
| Leaf width | Broad | Very narrow to narrow | Broad |

TABLE 1-continued

| Comparison of 'C15-270' with similar cultivars | | | |
|---|---|---|---|
| Characteristics | 'C15-270' | 'C99-042' (U.S. Plant Pat. No. 20,695P2) | 'Snowchaser' (U.S. Plant Pat. No. 19,503P3) |
| Leaf width (mm) | 34.6 ± 1.4 | 22.9 ± 1.3 | 34.3 ± 1.5 |
| Flower size of corolla | Small to medium | Medium | Medium |
| Flower corolla length (mm) | 8.8 ± 0.3 | 9.7 ± 0.3 | 9.5 ± 0.3 |
| Fruit cluster density | Dense | Sparse | Medium |
| Fruit size | Large | Small to medium | Small to medium |
| Fruit weight (g) | 3 ± 0.3 | 1.9 ± 0.39 | 1.7 ± 0.21 |
| Fruit diameter (mm) | 18.9 ± 1.3 | 15.6 ± 0.96 | 15.10 ± 0.97 |
| Fruit intensity of bloom | Medium | Weak to medium | Weak to medium |
| Fruit firmness | Very firm | Firm | Soft |
| Soluble solid content (%) | 13 | 13.1 | 14.3 |
| Titratable acidity (%) | 0.4 | 0.3 | 0.5 |
| Time of vegetative bud burst | Late | Early | Early |
| Time of beginning of flowering | Late | Early to medium | Very early to early |
| Time of beginning of fruit ripening | Late | Early to medium | Very early to early |

Table 2 below provides a comparison between 'C15-270' and 'C15-268':

TABLE 2

| Comparison of 'C15-270' with 'C15-268' | | |
|---|---|---|
| Characteristics | 'C15-270' | 'C15-268' (U.S. Plant Application No. 17/803,048) |
| Mature cane width (mm) | 15.8 | 14.1 |
| Fall color on new shoots | The base color is green group, similar to 137C and with over color, red-purple group 59A | Green group, similar to 138A, and with no noticeable over color |
| Internode length on strong, new shoots (mm) | 33.3 | 36.0 |
| Leaf width | Broad | Narrow to medium |
| Fruiting wood (cm) in length | 39.0 | 42.0 |
| Fruit weight (g) | 3 ± 0.3 | 3.2 ± 0.5 |
| Fruit diameter (mm) | 18.9 ± 1.3 | 19.4 ± 1.2 |
| Fruit intensity of bloom | Medium | Very Strong |
| Fruit stem scar | Large in size and wet | Small and dry |
| Disease resistance | resistant to blue-berry leaf rust (*Thekopsora minima*) | Susceptible to blue-berry leaf rust (*Thekopsora minima*) |
| Titratable acidity (%) | 0.4 | 0.3 |
| Time of beginning of flowering | Late | Medium to late |
| Time of beginning of fruit ripening | Late | Medium to late |
| Time of beginning of flowering | Late | Early to medium |
| Fruit storage quality (days) | Low, average of 17 days | medium to long storage, average 25 days |

The invention claimed is:

1. A new and distinct variety of blueberry plant named 'C15-270', substantially as illustrated and described herein.

* * * * *

C15-270